United States Patent [19]

Graber

[11] 4,216,774
[45] Aug. 12, 1980

[54] MEDICAL PAD

[75] Inventor: Helen E. Graber, Lino Lakes, Minn.

[73] Assignee: Alegra Products, Inc., Long Lake, Minn.

[21] Appl. No.: 959,629

[22] Filed: Nov. 13, 1978

[51] Int. Cl.³ ............................................. A61F 13/18
[52] U.S. Cl. .................................................... 128/296
[58] Field of Search .................... 128/155–156, 128/284, 287, 290 R, 292, 296; 5/90, 420, 473, 484, 502; 428/246, 251, 252, 282, 287

[56] References Cited

U.S. PATENT DOCUMENTS

| 1,533,973 | 4/1925 | Cohen et al. | 128/296 |
| 2,682,873 | 7/1954 | Evans et al. | 128/296 |
| 2,893,105 | 7/1959 | Lauterbach | 128/296 |
| 2,910,763 | 11/1959 | Lauterbach | 128/296 |
| 3,709,221 | 1/1973 | Riely | 128/156 |
| 3,888,257 | 6/1975 | Cook et al. | 128/296 |
| 3,967,623 | 7/1976 | Butterworth et al. | 128/287 |
| 3,993,828 | 11/1976 | McCorsley | 428/287 |
| 4,051,848 | 10/1977 | Levine | 128/156 |
| 4,077,410 | 3/1978 | Butterworth et al. | 128/156 |

Primary Examiner—C. Fred Rosenbaum

[57] ABSTRACT

Reusable, washable incontinent care medical pad including a top layer of soft, nonabrasive material, a second inner layer of maximum absorbency and softness material, a third inner layer of structural support material for stitching of the first, second and third layers, a fourth layer for one hundred percent liquid repellent material, all of the four layers being in alignment, and a binding material stitched to bind the first through fourth layers together along the outer perimeter. The first through third layers are stitched together in horizontal and vertical directions to provide support between the first through third layers.

2 Claims, 2 Drawing Figures

MEDICAL PAD

BACKGROUND OF THE INVENTION

1. Field of the Invention

The present invention relates generally to a medical pad, and more particularly, pertains to an incontinent care medical pad.

2. Description of the Prior Art

Those concerned with medical pads have long recognized the need for an incontinent care medical pad. The present invention fulfills this need.

The prior art medical pads have failed to provide an incontinent pad for protection not only to the patient but to the physical surroundings of the patient. The prior art pads were not comfortable to the patient, were not absorbent and soft to the patient, and could not be easily machined washed and dried by laundries, such as institutional laundries. Also, the prior art medical pads were not reusable through washings and failed to provide proper sanitary protection to the patient as well as the physical surroundings of the patient.

The present invention provides an incontinent care medical pad that overcomes the disadvantages of the prior art medical pads.

SUMMARY OF THE INVENTION

The general purpose of this invention is to provide an incontinent care medical pad.

According to one embodiment of the present invention, there is provided an incontinent care medical pad having a first layer of soft, nonabrasive material, a second layer of absorbing and soft material, a third layer of structural support material, a fourth layer of liquid repellent material and a binding material surrounding the outer perimeter of all four aligned layers and stitched thereto. Crisscross hoizontal and vertical stitching binds together the first three layers. The first three layers provide protection to the incontinent, and the fourth layer provides protection to the physical surroundings of the incontinent.

One significant aspect and feature of the present invention is that the incontinent pad is reusable through countless washings.

Having briefly described one embodiment of the present invention, it is a principal object hereof to provide an incontinent care medical pad.

An object of the present invention is to provide an incontinent care medical pad which is suitable for use in nursing homes, hospitals, and state and federal institutions. An incontinent is an individual who is incapable of holding back, containing or retaining the excretory functions.

Another object of the present invention is to provide an incontinent care medical pad which can be made of a size for a standard bed or for use in wheelchairs.

A further object of the present invention is an incontinent care medical pad which is washable and dryable using regular institutional laundry procedures, is of lightweight material to dry rapidly, and is reusable through countless washings.

A further object of the present invention is to provide an incontinent care medical pad which prevents chafing, feels warm even when wet to the patient, can be used to prevent decubidi, and a padding for heels, knees, etc. of an incontinent body. The incontinent pad does not bunch up but remains soft, dries quickly, and provides appropriate thickness for efficiency in bed changing and washing. Most importantly, the incontinent pad is designed to prevent liquid seepage through the pad into bed linens or other physical surrounding and prevents puddles on floors.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENT

Figure 1:
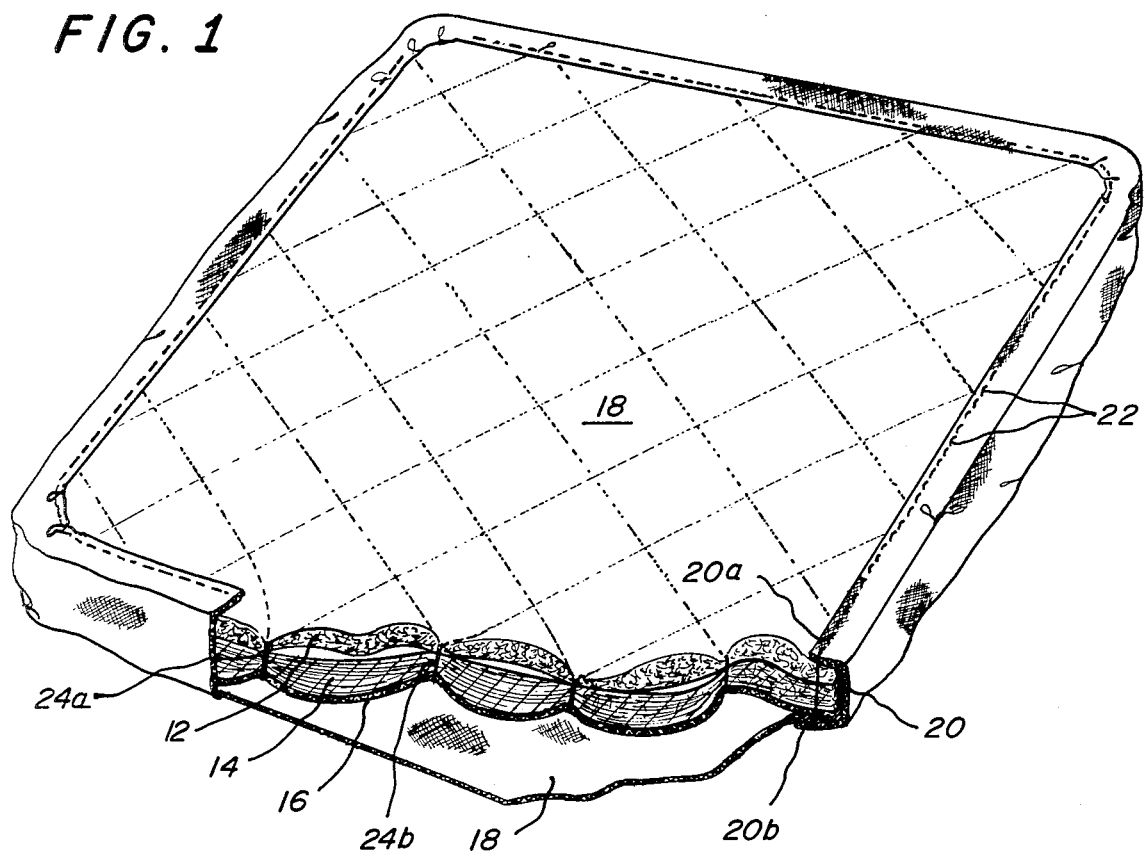
FIG. 1 illustrates a perspective view, partially cutaway, of an incontinent care medical pad, the present invention.

FIG. 1, which illustrates a perspective view, partially cutaway, of the incontinent care medical pad 10, the present invention, shows a first top layer 12 of soft, nonabrasive material to be positioned next to the clothing or skin of an incontinent person. A second inner layer of maximum absorbency and softness material 14 is positioned to coincide with the first top layer of material 12. A third inner layer 16 for structural support is positioned to coincide with the first and second layers 12 and 14 respectively. A fourth bottom layer 18 of one hundred percent liquid repellent nonabsorbent material is positioned to coincide with the first, second, and third layers 12, 14 and 16 respectively. A binding 20 surrounds the edges of the layers 12–18 respectively and overlaps the top layer 12 and the bottom layer 20. Stitching 22 surrounds the outer perimeter of the incontinent pad 10 and is stitched through the top 20a and the bottom 20b of the binding 20 and through the four layers 12–18 respectively. Horizontal and vertical stitching 24a and 24b respectively in a crisscross manner or any other suitable manner is stitched through the three layers 12, 14 and 16. The stitching does not go through the fourth layer 18 so as to prevent leakage.

Figure 2:
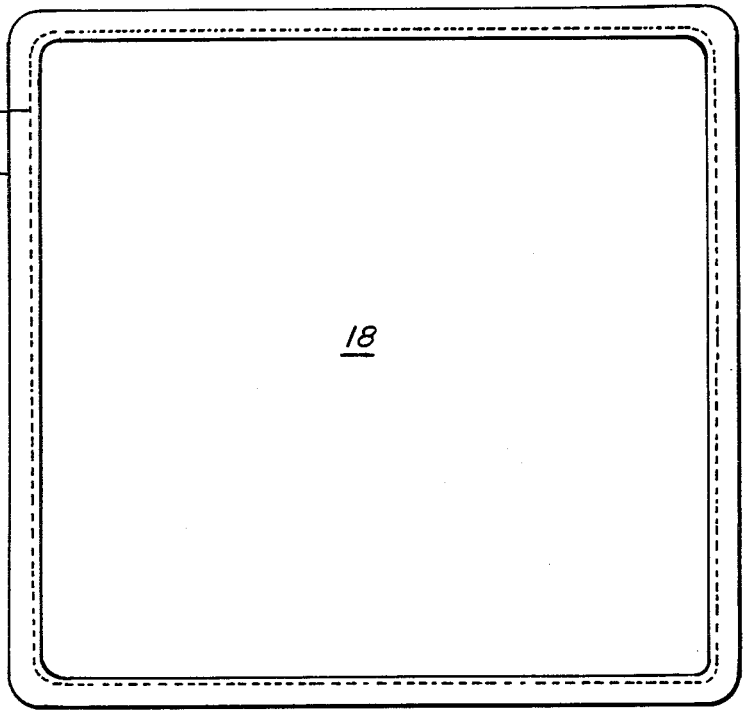
FIG. 2 illustrates a bottom view of the incontinent pad.

FIG. 2, which illustrates a bottom view of the incontinent pad 10, shows the fourth bottom layer 18 of liquid repellent material, the bottom 20a of the binding 20, and the bottom of the outer perimeter stitching 22.

PREFERRED MODE OF OPERATION

The incontinent care medical pad 10 can be manufactured any size such as twenty-four inches by thirty-six inches for complete protection of the standard hospital bed or eighteen inches by eighteen inches for use in a wheelchair. In cleaning, the incontinent care medical pad 10 can be washed and dried using regular institutional laundry procedures, and is manufactured of lightweight materials which dry rapidly. The incontinent care medical pad 10 is reusable through countless washings.

The incontinent care medical pad 10 is suggested for use as a reusable, washable pad for nursing homes, hospitals, and state and federal institutions. The top first layer 12 is soft, nonabrasive material which is positioned next to the patient's skin to prevent chafing, decubidi, feels warm even when wet, and can be used as padding for heels, knees, etc. One such suggested suitable material is Thermoslim TM, manufactured by J. P. Stevens Company, which is a one hundred percent polyester material which does not absorb moisture; does not shift, flatten or lump after washings, and has millions of tiny air pockets. The second inner layer 14 is chosen for maximum absorbency and softness and can be six to eight ounce polyester material which does not bunch up, remains soft, dries quickly, and is of the appropriate thickness for efficiency in bed changing and washing. The third inner layer 16 is provided for structural support for the vertical and horizontal cross stitching 24a and 24b, and can be a suitable material such as polyester or fiberglass. The fourth bottom layer 18 is one hundred percent liquid repellent waterproof oxford nylon material which is chemically treated and designed to prevent liquid seepage into or onto bed linens and wheelchair seats. The bottom layer 18 provides complete protection and no other protection of padding is required. The binding 20 can also be the waterproof oxford nylon material, the same material as the bottom layer 18. The four layers 12–18 have the same outer perimeter dimensions to align with each of the other layers 12–18.

Various modifications can be made to the incontinent care medical pad 10 without departing from the apparent scope of the invention.

Having thus described the invention, what is claimed is:

1. A medical pad for incontinent use comprising:
    a. a first top layer of one hundred percent polyester material having softness and nonabrasive qualities;
    b. a second inner layer to align with said first top layer of absorbing material of bonded six to eight ounce polyester;
    c. a third inner layer to align with said first and second layers of fiberglass structural material;
    d. a fourth layer of liquid repellent waterproof oxford nylon material to align with said first, second and third layers;
    e. binding liquid repellent waterproof oxford nylon material surrounding the outer perimeter edges of said first, second, third and fourth layers;
    f. first stitching between the top and bottom of said binding and through the four layers to bind the four layers together, and;
    g. second vertical and horizontal crisscross stitching the first, second and third pads together whereby said second stitching of the first, second and third pads together prevents bunching and movement of the first, second and third pads, and said first stitching of the four pads together thereby provides a medical pad which is warm even when wet to a patient on the top of said pad and prevents leakage through the bottom of said pad onto physical facilities.

2. A washable and reusable medical pad for incontinent use, comprising
    a. a first top layer of soft, nonabrasive polyester fabric material;
    b. a second inner layer of moisture absorbing material including six to eight ounce polyester;
    c. a third inner layer of structural supporting fabric material suitable for stitching therethrough;
    d. a fourth bottom layer of liquid repellent waterproof material;
    e. a quilted stitching pattern across and through the first, second and third layers, but not through the fourth layer; and
    f. an edge binding of liquid repellent waterproof material extending around the periphery and stitched through all four layers; whereby the fourth layer is attached to the first, second and third layers only along said periphery.

* * * * *